(12) United States Patent
Wilhelm

(10) Patent No.: US 11,160,942 B2
(45) Date of Patent: Nov. 2, 2021

(54) BREATHING BAG, SYSTEM COMPRISING A BREATHING BAG AND A DISPENSING VALVE UNIT, CLOSED-CIRCUIT RESPIRATOR AS WELL AS PROCESS FOR MOUNTING A SYSTEM COMPRISING A BREATHING BAG AND A DISPENSING VALVE UNIT IN A CLOSED-CIRCUIT RESPIRATOR

(71) Applicant: Dräger Safety AG & Co. KGaA, Lübeck (DE)

(72) Inventor: Christian Wilhelm, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 511 days.

(21) Appl. No.: 16/217,447

(22) Filed: Dec. 12, 2018

(65) Prior Publication Data

US 2019/0184117 A1 Jun. 20, 2019

(30) Foreign Application Priority Data

Dec. 14, 2017 (DE) ...................... 10 2017 011 583.4

(51) Int. Cl.
*A62B 7/10* (2006.01)
*A61M 16/00* (2006.01)
(Continued)

(52) U.S. Cl.
CPC .... *A61M 16/0078* (2013.01); *A61M 16/0891* (2014.02); *A61M 16/201* (2014.02);
(Continued)

(58) Field of Classification Search
CPC ............ A61M 16/201; A61M 16/0891; A61M 16/204; A61M 16/1005; A62B 7/00; A62B 7/10; A62B 9/00
See application file for complete search history.

(56) References Cited

U.S. PATENT DOCUMENTS

| 1,839,980 A | 1/1932 | Luchs et al. |
| 4,364,384 A | 12/1982 | Adalbert |
| 5,199,425 A * | 4/1993 | Perrier .................... B63C 11/24 |
| | | 128/204.26 |

FOREIGN PATENT DOCUMENTS

| CN | 101115521 A | 1/2008 |
| CN | 203677780 U | 7/2014 |

(Continued)

*Primary Examiner* — Margaret M Luarca
(74) *Attorney, Agent, or Firm* — McGlew and Tuttle, P.C.

(57) ABSTRACT

A breathing bag (20) has a tray section (21) and a bag section (22). The tray section (21) and the bag section enclose an inner volume (24) of variable size, the bag section dipping at least partially into the tray section to reduce the size of the inner volume. A system (10) includes the breathing bag, for a closed-circuit respirator (100), with a dispensing valve unit (40) having a dispensing valve (41) providing a quantity of gas in a breathing circuit. An actuating unit (42) is functionally connected mechanically to the dispensing valve for actuating the dispensing valve. A lever component (50) is functionally connected mechanically to the actuating unit for activating the actuating unit. A closed-circuit respirator has the system including the breathing bag and the dispensing valve unit. A process is provided for mounting the system, including breathing bag and dispensing valve unit, in the closed-circuit respirator.

20 Claims, 3 Drawing Sheets

(51) Int. Cl.
*A61M 16/20* (2006.01)
*A61M 16/08* (2006.01)
A61M 16/10 (2006.01)
A61M 16/12 (2006.01)

(52) U.S. Cl.
CPC ......... *A61M 16/1005* (2014.02); *A61M 16/12* (2013.01); *A61M 16/204* (2014.02); *A61M 2202/0208* (2013.01); *A61M 2205/3306* (2013.01); *A61M 2205/3334* (2013.01); *A61M 2207/00* (2013.01); *A61M 2230/63* (2013.01)

(56) References Cited

FOREIGN PATENT DOCUMENTS

| | | |
|---|---|---|
| DE | 10 2014 017 954 A1 | 6/2016 |
| DE | 10 2014 017 954 B4 | 5/2018 |
| EP | 0221945 B1 | 11/1992 |

* cited by examiner

BREATHING BAG, SYSTEM COMPRISING A BREATHING BAG AND A DISPENSING VALVE UNIT, CLOSED-CIRCUIT RESPIRATOR AS WELL AS PROCESS FOR MOUNTING A SYSTEM COMPRISING A BREATHING BAG AND A DISPENSING VALVE UNIT IN A CLOSED-CIRCUIT RESPIRATOR

CROSS REFERENCE TO RELATED APPLICATIONS

This application claims the benefit of priority under 35 U.S.C. § 119 of German Application 10 2017 011 583.4, filed Dec. 14, 2017, the entire contents of which are incorporated herein by reference.

FIELD OF THE INVENTION

The present invention pertains to a breathing bag for a closed-circuit respirator, having a tray section and a bag section, wherein the tray section and the bag section enclose an inner volume of variable size, and wherein the bag section further dips at least temporarily at least partially into the tray section during a reduction of the size of the inner volume. The present invention further pertains to a system comprising a breathing bag and a dispensing valve unit for a closed-circuit respirator, the dispensing valve unit having a dispensing valve for providing a quantity of gas in a breathing circuit of the closed-circuit respirator and an actuating unit connected mechanically functionally to the dispensing valve for actuating the dispensing valve, the system further comprising a lever component, which is mechanically functionally connected to the actuating unit for actuating the actuating unit. Moreover, the present invention pertains to closed-circuit respirator, having a system comprising a breathing bag and a dispensing valve unit as well as to a process for mounting a system comprising a breathing bag and a dispensing valve unit in a closed-circuit respirator.

BACKGROUND OF THE INVENTION

Closed-circuit respirators are basically known and are often used under very difficult conditions in order to make it possible to provide especially an ambient air-independent breathing air supply for a user of a closed-circuit respirator. Areas and conditions of use of closed-circuit respirators are, for example, in firefighting as part of equipment of firefighters, but also in mine rescue. Prior-art closed-circuit respirators have as the central component a counter-lung with a breathing bag. Additional components of closed-circuit respirators may be, for example, filter units, especially $CO_2$ filters, as well as air conditioning units and an oxygen source.

The breathing bag of a closed-circuit respirator is used mostly as a collection volume or active gas reservoir for the air exhaled by a user of the closed-circuit respirator, from which the carbon dioxide had been removed. Prior-art breathing bags enclose an inner volume, whose size changes continually due to a cyclic inflation and collapse. A quantity of gas can be taken up in the breathing bag due to the inflation, and a quantity of gas can be released from the breathing bag due to the collapse of the inner volume. Prior-art breathing bags usually have a tray section and a bag section, which adjoin each other and move relative to one another during the cyclic change in the size of the inner volume. The bag section usually dips at least partially into the tray section in case of a minimal inner volume during this motion.

To prevent an excessively small inner volume and hence in the worst case an interruption of the breathing air supply for a user of the closed-circuit respirator, it is further known that a dispensing valve or at least the actuating mechanism of a dispensing valve can be arranged in the breathing bag to provide and/or ensure a minimal quantity of breathing air. At the same time, tightness of the breathing bag is decisive, in particular, for the satisfactory functioning of the breathing bag and hence of the entire closed-circuit respirator. Complicated sealing procedures are thus necessary to seal the dispensing valve unit or at least the actuating mechanism of the dispensing valve unit at the breathing bag against the surrounding area. Moreover, comprehensive cleaning and/or disinfection of all the components of the closed-circuit respirator that come into contact with breathing air is necessary at least after each use for a satisfactory operation of the closed-circuit respirator. In prior-art closed-circuit respirators, this comprises especially also the dispensing valve unit and its actuating components. The regular maintenance of and care for a closed-circuit respirator is, as a result, often complicated and also error-prone, especially if it is performed improperly.

SUMMARY OF THE INVENTION

Based on this background art, a basic object of the present invention is to at least partially eliminate these drawbacks of breathing bags for closed-circuit respirators, of systems comprising a breathing bag and dispensing valve units, of closed-circuit respirators as well as of processes for mounting a system comprising a breathing bag and a dispensing valve unit in a closed-circuit respirator. Therefore, an object of the present invention is to provide a breathing bag, a system comprising a breathing bag and a dispensing valve unit, a closed-circuit respirator as well as a process for mounting such a system in a closed-circuit respirator, which comprise a simplified breathing bag in as simple and cost-effective manner as possible, wherein especially the provision of a minimal quantity of breathing gas can be ensured for a user of the closed-circuit respirator at any time and the manufacture and the maintenance of a closed-circuit respirator with such a breathing bag can at the same time be simplified.

The above object is accomplished by a breathing bag for a closed-circuit respirator having the features according to the invention. The object is further accomplished by a system comprising a breathing bag and a dispensing valve unit for a closed-circuit respirator having the features described according to the invention. Moreover, the object is accomplished by a closed-circuit respirator having the features according to the invention as well as by a process for mounting a system comprising a breathing bag and a dispensing valve unit having the features according to the invention. Further features and details of the present invention appear from the description and from the drawings. Features and details that are described in connection with the breathing bag also apply, of course, in connection with the system according to the present invention, the closed-circuit respirator according to the present invention as well as the method according to the present invention and vice versa, so that reference is and can always mutually be made to the individual aspects of the present invention concerning the disclosure.

According to a first aspect of the present invention, the object is accomplished by a breathing bag for a closed-circuit respirator, having a tray section and a bag section, wherein the tray section and the bag section enclose an inner volume of variable size, and wherein the bag section further dips at least temporarily at least partially into the tray section during a reduction of the size of the inner volume. A breathing bag according to the present invention is characterized in that the tray section has a pocket with an internal receptacle for receiving a lever component for actuating an actuating unit of a dispensing valve unit of the closed-circuit respirator, wherein the pocket protrudes with the internal receptacle into the inner volume and the internal receptacle is separated from the inner volume in a gas-tight manner and is further accessible from the outside of the breathing bag.

A breathing bag according to the present invention is intended for use in a closed-circuit respirator. The breathing bag according to the present invention has, as a central component of the closed-circuit respirator, a tray section and a bag section, which preferably adjoins same, which together enclose an inner volume. The breathing bag especially preferably comprises at least essentially the tray section and the bag section. The inner volume can assume variable sizes during the use of the closed-circuit respirator, and this change in the size of the inner volume can be made possible especially by an unfolding and folding in of the bag section in relation to the tray section. The breathing bag thus represents a variable gas reservoir, in which breathing gas can be stored and kept in reserve for a user of the closed-circuit respirator.

Provisions are made according to the present invention in a breathing bag according to the present invention for the tray section to have a pocket with an internal receptacle. The tray section usually represents the lower area of the breathing bag, which does not preferably participate in the change in the size of the variable inner volume or does so at least only slightly. In other words, the tray section may have a more rigid, more stable and more inflexible configuration than the bag section, as a result of which it is especially suitable for arranging junction sections and hence also for the pocket according to the present invention.

The pocket is especially configured such that the pocket protrudes into the inner volume. In other words, the pocket begins at a wall area of the tray section and extends away from the wall area into the inner volume of the breathing bag. An internal receptacle, which is intended especially for receiving a lever component, is arranged in the interior of the pocket. This lever component is used, in turn, in a closed-circuit respirator, for example, to actuate an actuating unit of a dispensing valve unit. In other words, an actuating unit of a dispensing valve unit of the closed-circuit respirator can be activated and actuated by means of a deflection of the lever component, which is arranged in the internal receptacle of the pocket. Such a dispensing valve unit usually has especially a dispensing valve, by which a minimal quantity of breathing air can be ensured in a breathing circuit for a user of the closed-circuit respirator by correspondingly feeding a quantity of gas, especially, e.g., oxygen into the breathing circuit.

As an essential feature of the present invention, provisions are made, furthermore, for the internal receptacle of the pocket to be separated from the inner volume in a gas-tight manner. In other words, no gas exchange can take place between the inner volume of the breathing bag and the internal receptacle of the pocket; in particular, the internal receptacle preferably has a gas-tight configuration against the inner volume. Moreover, the internal receptacle is, however, accessible from the outside of the breathing bag. This makes it possible, in particular, to push the lever component into the internal receptacle from the outside of the breathing bag for actuating the actuating unit of the dispensing valve unit. It can be made possible in this manner that the lever component likewise protrudes in the interior of the internal receptacle into the inner volume of the breathing bag, without, however, having to directly assume a fluid-communicating state to the inner volume.

In summary, it can thus be made possible by a breathing bag according to the present invention that an actuating unit of a dispensing valve unit can be actuated by actuating a lever component, without this lever component or another component of the dispensing valve unit having to come into direct contact with the inner volume of the breathing bag and with the breathing gas contained therein. It can be made possible hereby that, for example, the pocket is contacted by the bag section in the interior of the inner volume by the bag section dipping into the tray section in case of a minimally possible (allowable) inner volume, and the lever component is actuated thereby at the same time. Actuation of the dispensing valve of the dispensing valve unit can be made possible in this manner. At the same time, provisions may be made by the gas-tight configuration of the pocket for the lever component and the entire dispensing valve unit to be able to be arranged outside the breathing bag, particularly outside the inner volume. Complicated cleaning and disinfection operations during maintenance procedures on the closed-circuit respirator can as a result be simplified or even become unnecessary. Further, the manufacture and the assembly of the closed-circuit respirator can also be simplified due to this arrangement of the entire dispensing valve unit and of the lever component outside the breathing bag, because complicated sealing procedures and testing procedures for testing the tightness of the breathing bag to ensure that the dispensing valve unit is arranged correctly and in a gas-tight manner in and/or at the breathing bag can be avoided.

Provisions may especially preferably be made in a breathing bag according to the present invention for the pocket to have a flexible configuration in at least some sections. It can be ensured in this manner in an especially simple manner that, for example, a deflection of the pocket and hence a deflection of the lever component arranged in the internal receptacle of the pocket can be generated in case of a contact of the pocket with the bag section in case of a minimal inner volume. A functionality of the pocket as a mounting location for the lever component can be made possible in this manner without limiting the functionality of the lever component as an actuating unit of the dispensing valve unit.

Further, provisions may be made in a breathing bag according to the present invention for the pocket to have a contact surface on a surface facing the inner volume for contacting by a counter-contact section of the bag section. This contact section may have special properties that are especially advantageous for contacting the counter-contact section of the bag section. For example, the contact section may thus have a more stable configuration than the rest of the pocket in order not to be damaged by the intended contact with the counter-contact section of the bag section. The contact section may also have, for example, a slight roughness in order to prevent the contact section from adhering to the counter-contact section.

According to a variant, a breathing bag according to the present invention may further be configured such that the contact section has a projecting releasing component. Such a releasing component may be used, for example, to define and provide a contact point between the contact section and the counter-contact section of the bag section. A contact that can be planned especially accurately between the contact section and the counter-contact section and hence an actuation of the downstream actuating unit of the dispensing valve unit, which actuation can be set especially well, can be made possible in this manner.

Provisions may, further, also be made in a breathing bag according to the present invention for the pocket to have a tapering configuration along a longitudinal extension in the inner volume. In other words, the pocket may have a larger cross section at a pocket base, which is arranged at a wall area of the tray section, than at a pocket tip in the interior of the inner volume. Sufficient stability of the entire pocket and of the lever component arranged therein can be made possible by this larger cross section at the base, and the volume displaced in the inner volume by the pocket can at the same time be minimized due to the tapering along the longitudinal extension.

The breathing bag according to the present invention may also be configured such that the lever component is a component of the breathing bag and is fastened in the internal receptacle by connection in substance. In other words, provisions are made in this embodiment of a breathing bag according to the present invention for the lever component to form a part of the breathing bag. This may accompany, for example, a lever mount or a fulcrum point of the lever component being arranged in the interior or at least at the edge of the breathing bag. An especially compact breathing bag can be provided due to such a one-piece configuration of the breathing bag and of the lever component. An arrangement of the lever component in the internal receptacle by connection in substance represents an especially preferred fastening or arrangement of the lever component in the internal receptacle of the pocket.

A breathing bag according to the present invention may be improved such that the lever component is welded and/or bonded and/or vulcanized to the internal receptacle. Welding and/or bonding and/or vulcanization proved to be especially suitable for fastening a lever component in the internal receptacle by connection in substance. Regardless of this, other methods of connection in substance may be used as well to arrange the lever component in the internal receptacle, insofar as these are technically meaningful and possible.

According to an alternative embodiment of a breathing bag according to the present invention, this bag may further be improved such that the pocket and the lever component are manufactured together in a multicomponent injection molding process. It can be made possible in this manner, for example, that the molded lever component is manufactured from a different material than the molded pocket enclosing the molded lever component. Nevertheless, the lever component can be manufactured by the multicomponent injection molding process in the same manufacturing process step and hence monolithically with the pocket and hence with the tray section of the breathing bag. A molded configuration, manufactured by a multicomponent injection molding, process may also be provided in the sense of the present invention, in which configuration the pocket only represents a frame of the lever component made of the material of the tray section in the wall area of the tray section at the base of the lever component and the lever component, manufactured from another, especially more rigid, material, extends into the inner volume without an additional jacketing. On the whole, an especially simple, rapid and consequently time- and cost-saving type of manufacturing a breathing bag according to the present invention can be made possible by the use of a multicomponent injection molding process.

According to a second aspect of the present invention, the object is accomplished by a system comprising a breathing bag and a dispensing valve unit for a closed-circuit respirator, the dispensing valve unit having a dispensing valve for providing a quantity of gas in a breathing circuit of the closed-circuit respirator and an actuating unit functionally connected mechanically to the dispensing valve for actuating the dispensing valve, the system further having a lever component, which is functionally connected mechanically to the actuating unit for activating the actuating unit. A system according to the present invention is characterized in that the breathing bag is configured according to the first aspect of the present invention, wherein the lever component is arranged in the internal receptacle of the pocket. All the advantages that are described in detail in reference to a breathing bag according to the first aspect of the present invention can thus also be made possible by a system according to the second aspect of the present invention, which system has such a breathing bag according to the first aspect of the present invention.

A system according to the present invention, comprising a breathing bag and a dispensing valve unit, can provide especially the functionality that activation of the dispensing valve of the dispensing valve unit can be performed when the quantity of breathing air drops below a minimal quantity in the breathing bag. This can be made possible, for example, by a bag section of the breathing bag dipping so deeply into the tray section of the breathing bag that it actuates the lever component arranged in the internal receptacle of the pocket of the tray section. Due to the mechanical functional connection of the lever component with the actuating component, the actuating unit is, in turn, activated, and this unit will then actuate the dispensing valve in order to feed a certain quantity of gas, for example, oxygen, into a breathing circuit of the closed-circuit respirator. The quantity of breathing gas in the breathing circuit of a user of the closed-circuit respirator can be prevented in this manner from dropping below a minimally present quantity of breathing gas.

According to a first preferred embodiment of a system according to the present invention, provisions may be made for the lever component to be a part of the actuating unit. It can be made possible in this manner, for example, to configure the actuating unit and hence the entire dispensing valve unit in an especially compact and space-saving form. Due, in particular, to the possibility of eliminating connection components between the actuating unit and the lever component, it is possible to provide this especially compact configuration of the dispensing valve unit.

In a likewise preferred embodiment, provisions may be made in case of a system according to the present invention for the lever component to be a component of the breathing bag. Thus, the lever component may already be fastened, for example, by connection in substance in the internal receptacle of the pocket or even fastened monolithically with this pocket, for example, by a multicomponent injection molding process. An especially compact configuration of the breathing bag can be provided, in turn, in this embodiment. Depending on the location and purpose of use, it is possible to use, in particular, the more fitting alternative embodiment of a system according to the present invention.

Moreover, provisions may be made in a system according to the present invention for the actuating unit to be configured for the continuous or at least essentially continuous control of the quantity of gas provided by the dispensing valve as a function of the deflection of the lever component. A deflection of the lever component may be defined, in particular, as a deflection from a resting and/or normal position of the lever component. As an alternative or in addition, provisions may be made for a certain quantity of gas to be already provided by the dispensing valve in the resting or normal position. It is essential in this embodiment of a system according to the present invention, in particular, that the provision of the quantity of gas follows a deflection of the lever component continuously or at least essentially continuously. In other words, a larger quantity of gas can thus also be provided in case of a greater deflection of the lever component. The quantity of gas can thus be supplied especially correctly according to the need.

Further, the system according to the present invention may be configured such that the dispensing valve has a junction section for providing the quantity of gas at a feed point located at a distance from the breathing bag into the breathing circuit of the closed-circuit respirator. In particular, the feed point can be selected at any desired and especially freely selectable feed point into the breathing circuit due to the presence of this junction section. An especially flexible feed of the quantity of gas provided into the breathing circuit of the closed-circuit respirator can be made possible in this manner.

Moreover, provisions may further be made in a system according to the present invention for the dispensing valve unit to have a fastening section for fastening on a counter-fastening section of the closed-circuit respirator, especially of a housing of the closed-circuit respirator. It can, in particular, be made possible in this manner to arrange, especially to fasten, the dispensing valve unit permanently in the closed-circuit respirator. It may be, in particular, advantageous that the dispensing valve unit can first be arranged and fastened together with the lever component, for example, in a housing of the closed-circuit respirator, for example, during the mounting of the closed-circuit respirator, and the breathing bag and the internal receptacle of the pocket of the breathing bag are pushed over, in a second step, for arranging and fastening the breathing bag in the closed-circuit respirator via the lever component. The assembly of the breathing bag and of the entire system can be simplified in this manner.

Further, provisions may be made in a system according to the present invention for the dispensing valve unit to have a sensor unit for monitoring the actuation of the dispensing valve. Data on the actuation of the dispensing valve can be obtained in this manner in order to determine, for example, the respiration rate of a user of the closed-circuit respirator. This can make it possible to calculate run times and/or operation times. Moreover, the data determined may also be used for the physiological monitoring of the user of the closed-circuit respirator.

According to a variant of a system according to the present invention, provisions may further be made for the sensor unit to have at least one of the following sensor components:
  Hall sensor,
  optical sensor,
  motion sensor,
  gas flow sensor.

This list is not complete, in particular, so that other sensor components may also be used in the sensor unit insofar as technically meaningful and possible.

According to a third aspect of the present invention, the object is accomplished by a closed-circuit respirator, having a system comprising a breathing bag and a dispensing valve unit. A closed-circuit respirator according to the present invention is characterized in that the system is configured according to the second aspect of the present invention. A system according to the second aspect of the present invention has, in particular, a breathing bag according to the first aspect of the present invention. A closed-circuit respirator according to the present invention according to the third aspect of the present invention may thus have all the advantages that were already described in detail in reference to a breathing bag according to the first aspect of the present invention as well as in reference to a system according to the second aspect of the present invention.

According to a fourth aspect of the present invention, the object is accomplished by a process for mounting a system comprising a breathing bag and a dispensing valve unit in a closed-circuit respirator according to the third aspect of the present invention. A process according to the present invention is characterized by the following steps:
  a) Arrangement and fastening of the dispensing valve unit and of the lever component in the closed-circuit respirator, and
  b) insertion of the breathing bag into the closed-circuit respirator by pushing the internal receptacle of the pocket of the breathing bag over the lever component.

A process according to the present invention is configured for mounting a system comprising a breathing bag and a dispensing valve unit in a closed-circuit respirator according to the third aspect of the present invention. The mounted system is thus preferably configured according to the second aspect of the present invention and has, in particular, a breathing bag according to the first aspect of the present invention. All the advantages, which were described in detail in reference to a breathing bag according to the first aspect of the present invention; in reference to a system according to the second aspect of the present invention; as well as in reference to a closed-circuit respirator according to the third aspect of the present invention, can thus also be ensured by a process according to the fourth aspect of the present invention.

In a first step a) of a process according to the present invention, a dispensing valve unit of a system according to the present invention and additionally a lever component are arranged and fastened in the closed-circuit respirator. In other words, the lever component may be configured as a part of the dispensing valve unit in this embodiment of a process according to the present invention. After carrying out step a) of a process according to the present invention, the dispensing valve unit is, in particular, fastened permanently in the closed-circuit respirator, for example, in a housing of the closed-circuit respirator. This makes possible, in a second step b) of a process according to the present invention, a simple insertion of the breathing bag such that the lever component, which is already installed permanently, is used to push or pull the internal receptacle of the pocket of the breathing bag over the lever component. Since, as was described above, the lever component is already arranged permanently in the closed-circuit respirator, the breathing bag can be arranged in the closed-circuit respirator in this manner in an especially simple manner and especially at an accurate location. Additional fastening procedures for the breathing bag, especially also at the dispensing valve unit, may further support this arrangement and fastening of the breathing bag in the closed-circuit respirator.

Further actions improving the present invention appear from the following description of exemplary embodiments of the present invention, which are shown in the figures. All the features and/or advantages appearing from the claims, from the description and from the drawings, including design details and arrangements in space, may be essential for the present invention both in themselves and in the different combinations. Components having the same function and mode of action are designated by the same reference numbers in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
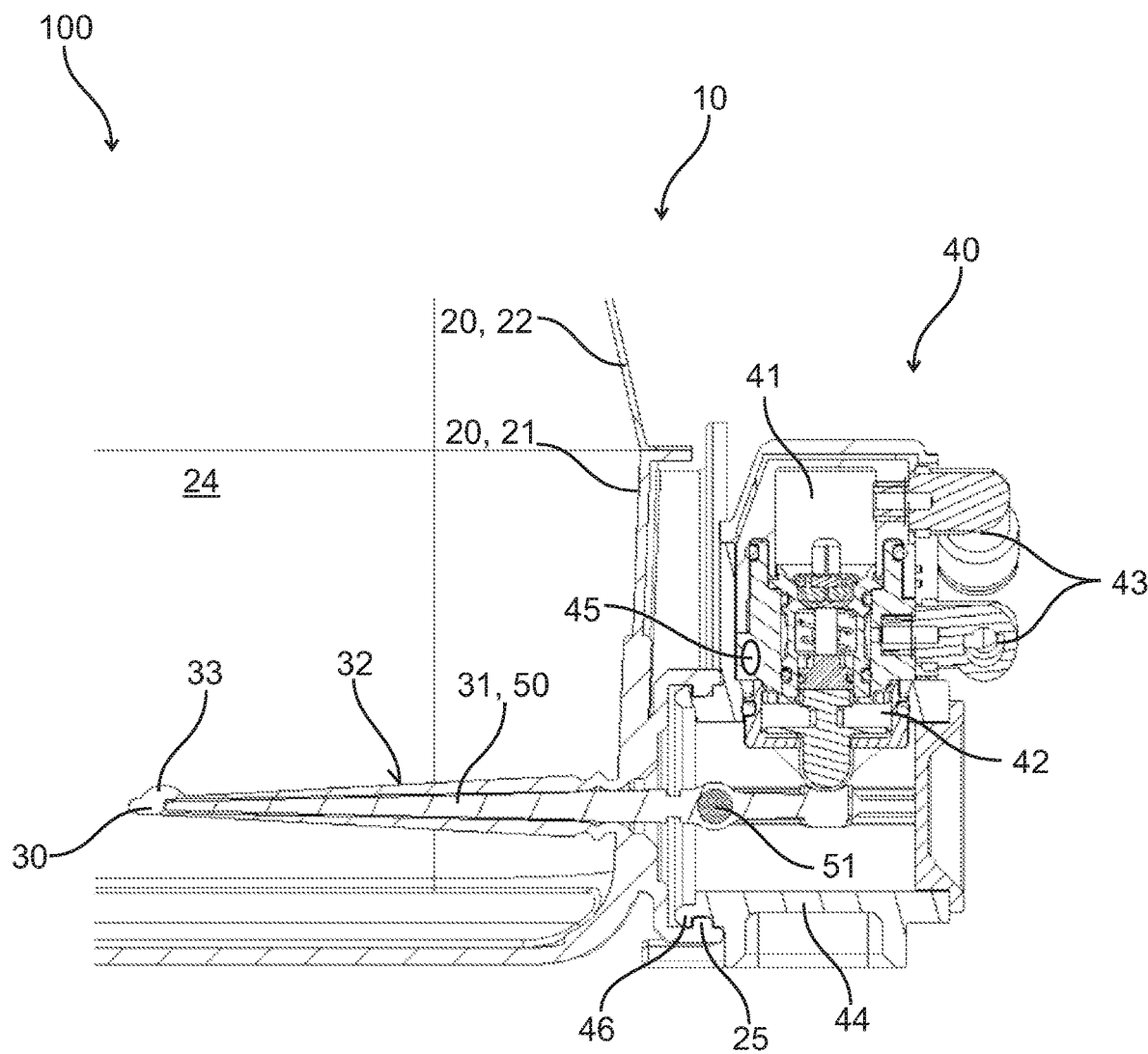
FIG. 1 is a sectional view showing a system according to the present invention of a closed-circuit respirator in a sectional view.
Figure 2:
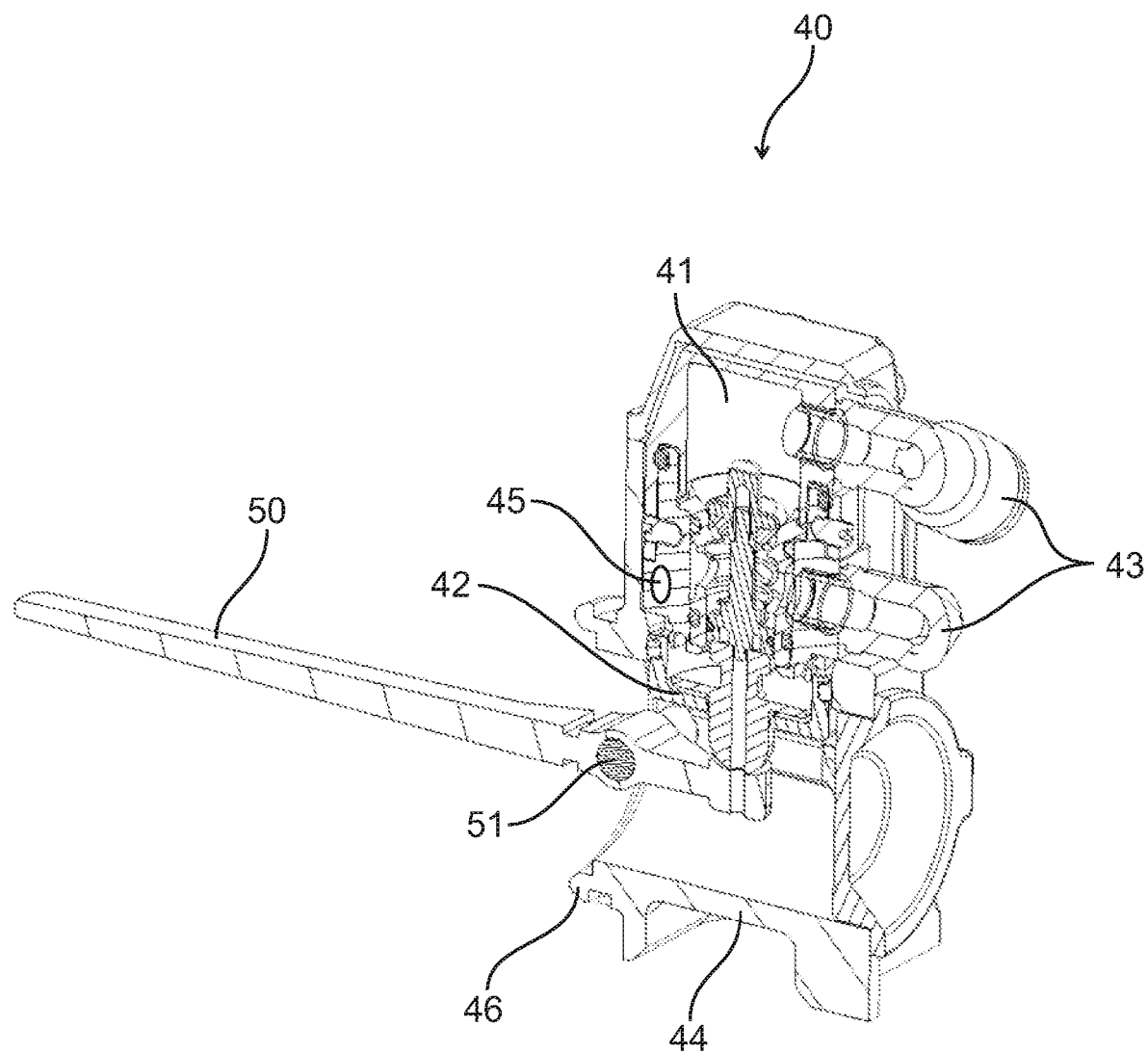
FIG. 2 is a perspective and partially sectional view of a dispensing valve unit.
Figure 3:
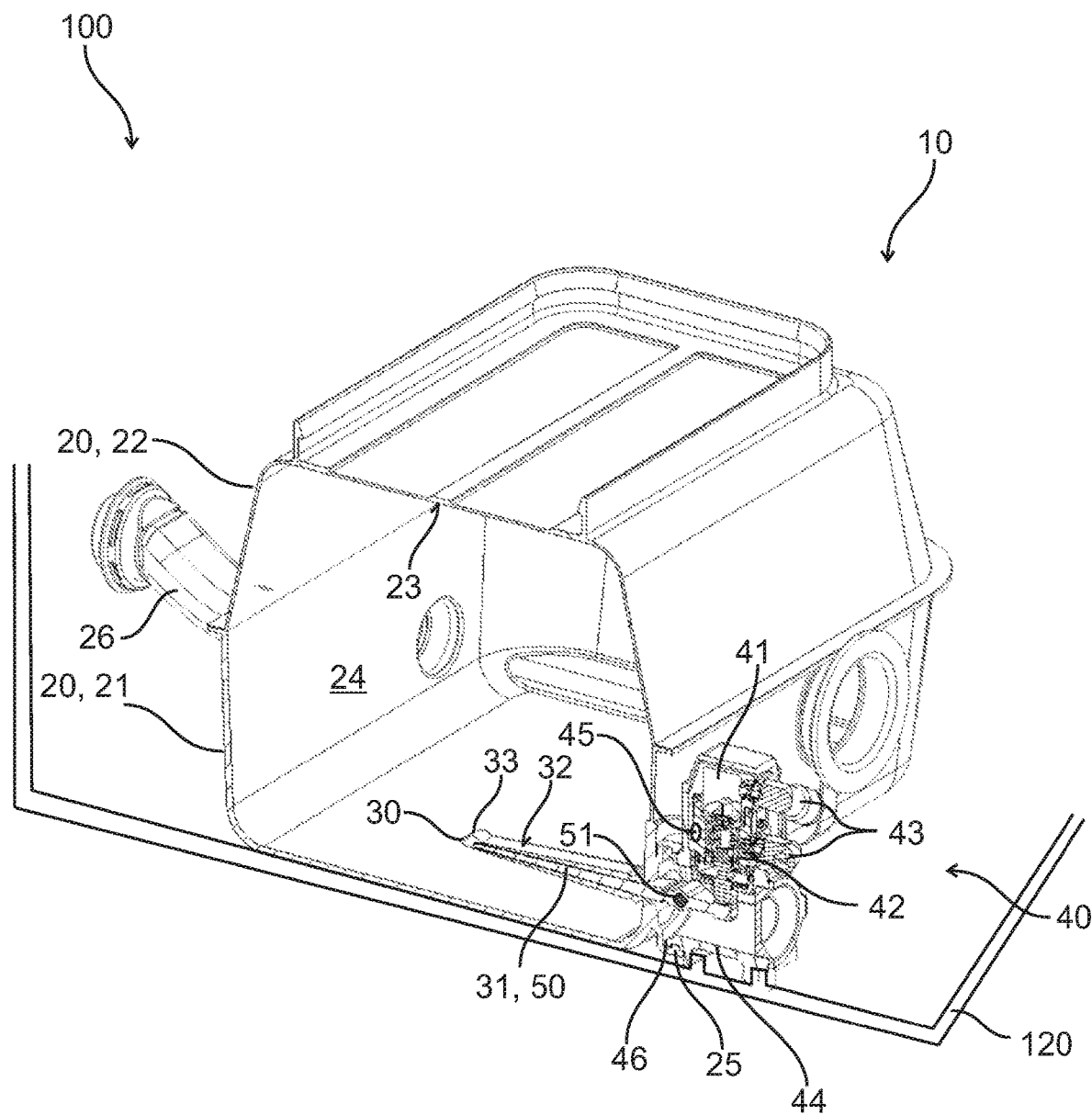
FIG. 3 is a perspective and partially sectional view of a system according to the present invention of a closed-circuit respirator.

Referring to the drawings, FIGS. 1 through 3 show different components of a closed-circuit respirator 100 according to the present invention and of a system 10 according to the present invention in different views. The figures will therefore be described together below, and corresponding details of the figures will be discussed separately.

In particular, FIG. 2 shows a possible embodiment of a dispensing valve unit 40, as it may be used in a system 10 according to the present invention, shown in FIGS. 1 and 3. In the embodiment shown, the lever component 50 is configured as a part of the dispensing valve unit 40. An actuating unit 42 of the dispensing valve unit 40 can be activated via a lever mount 51 in case of a deflection of the lever component 50 from a lever mount resting position shown. The actuating unit 42 does, in turn, actuate the dispensing valve 41 itself of the dispensing valve unit 40, as a result of which a quantity of gas can be released into a breathing circuit of the closed-circuit respirator 100. The dispensing valve unit 40 has, in particular, junction sections 43 for this purpose, which make it possible, as is shown in FIGS. 1 and 3, to feed the quantity of gas into the breathing circuit of the closed-circuit respirator 100 independently from the breathing bag 20. The actuating unit 42 is configured, in particular, such that corresponding to a position of the lever component 50, release of a continuous or at least essentially continuous quantity of gas into the breathing circuit of the closed-circuit respirator 100 can be made possible via the junction sections 43. An especially need-controlled release of the quantity of the gas can be made possible in this manner. A sensor unit 45, for example, a Hall sensor or an optical sensor, makes it possible to monitor the quantity of gas released and the functionality of the dispensing valve 41, as a result of which the functionality of the entire closed-circuit respirator 100 and also of physiological parameters of the user of the closed-circuit respirator 100 can be analyzed or monitored. The entire dispensing valve unit 40 may be arranged and fastened in a housing 120 of the closed-circuit respirator 100 by means of fastening sections 44. This makes possible an especially simple mounting of a system 10 according to the present invention comprising a breathing bag 20 and a dispensing valve unit 40 in the housing 120 of the closed-circuit respirator 100, wherein the dispensing valve unit 40 is arranged and fastened in the closed-circuit respirator 100 in a first step and the breathing bag 20 is simply pulled over the lever component 50 in a second step, as it is shown already after completion of this action in FIGS. 1 and 3. This can be made possible, in particular, by the tray section 21 of the breathing bag 20 having according to the present invention a pocket 30 with an internal receptacle 31.

This pocket 30 with the internal receptacle 31 is an essential part of the breathing bag 20 according to the present invention. In particular, this internal receptacle 31 is accessible, as is shown, from the outside of the breathing bag 20 and has at the same time a gas-tight configuration against the inner volume 24 of the breathing bag 20. An additional sealing of the lever component 50 or of the entire dispensing valve unit 40 against the inner volume 24 of the breathing bag 20 can be avoided in this manner. Additional locking sections 46 of the dispensing valve unit 40, which can interact with counter-locking sections 25 of the breathing bag 20, may further support the arrangement of the breathing bag 20 in the closed-circuit respirator 100. The system 10 according to the present invention is shown in FIGS. 1 and 3, in particular, as an interaction of the breathing bag 20 and the dispensing valve unit 40. In addition to the embodiment shown, in which the lever component 50 is configured as a part of the dispensing valve unit 40, the lever component 50 may, as an alternative, also be configured as a part of the breathing bag 20. Thus, the lever component 50 may be arranged, for example, by connection in substance, preferably welded, bonded and/or vulcanized, in the internal receptacle 31 of the pocket 30. A joint, monolithic manufacture of the pocket 30 and of the lever component 50, especially in a multicomponent injection molding process, may also be provided in an alternative embodiment of a system 10 according to the present invention.

The size of the inner volume 24 of the breathing bag 20 changes cyclically during an operation of the closed-circuit respirator 100. In particular, the bag section 22 and the tray section 21 of the breathing bag 20 may be configured such that the bag section 22 has a more flexible configuration than the tray section 21 and the cyclical change in the inner volume 24 is due at least essentially to folding-in and unfolding processes. Especially in case of especially small inner volumes 24 of the breathing bag 20, the bag section 22 dips at least partially into the tray section 21. It may now happen that especially in case of a minimal inner volume 24, a counter-contact section 23 of the bag section 22 contacts a contact section 32 of the pocket 30. This may occur first especially at a releasing component 33, which is configured for this purpose as a projecting component at the contact section 32.

On the whole, a deflection of the lever component 50, especially from a resting position of the lever component 50, can be generated by the contacting of the counter-contact section 23 at the contact section 32. This deflection of the lever component 50 is transmitted via the mechanical functional connections first to the actuating unit 42 and correspondingly via the actuating unit 42 to the dispensing valve 41. An additional feeding of a quantity of gas into a breathing circuit of the closed-circuit respirator 100 via the junction sections 43 of the dispensing valve 41 can be made possible in this manner especially in the minimal state of the inner volume 24 of the breathing bag 20. The quantity of gas can be prevented in this manner from dropping below a minimal quantity in the breathing circuit of the closed-circuit respirator 100. Deflection of the lever component 50 may be brought about and supported especially by the pocket 30 having a flexible configuration at least in some sections. Due to the preferred shape, as shown, of a tapering pocket 30, sufficiently high stability of the pocket 30 can be ensured, on the one hand, at the base of the pocket 30 at a wall area of the tray section 21, and the volume required in the inner volume 24 can at the same time be kept as small as possible due to the pocket 30. A reduction of the tidal volume in the breathing circuit of the closed-circuit respirator 100 can be minimized in this manner.

While specific embodiments of the invention have been shown and described in detail to illustrate the application of the principles of the invention, it will be understood that the invention may be embodied otherwise without departing from such principles.

Appendix:

LIST OF REFERENCE NUMBERS

10 System
20 Breathing bag
21 Tray section
22 Bag section
23 Counter-contact section
24 Inner volume
25 Counter-locking section
26 Drainage port
30 Pocket
31 Internal receptacle
32 Contact section
33 Releasing component
40 Dispensing valve unit
41 Dispensing valve
42 Actuating unit
43 Junction section
44 Fastening section
45 Sensor unit
46 Locking section
50 Lever component
51 Lever mount
100 Closed-circuit respirator
120 Housing

What is claimed is:

1. A breathing bag for a closed-circuit respirator comprising a dispensing valve unit, the breathing bag comprising:
a tray section;
a bag section, wherein the tray section and the bag section enclose an inner volume of variable size and wherein the bag section is configured to dip at least temporarily and at least partially into the tray section, providing a reduction in the size of the inner volume, wherein the tray section comprises a pocket with an internal receptacle for receiving a lever component for actuating an actuating unit of the dispensing valve unit of the closed-circuit respirator, wherein the pocket with the internal receptacle protrudes into the inner volume and the internal receptacle is separated from the inner volume in a gas-tight manner and the internal receptacle is furthermore accessible from an outside of the breathing bag.

2. A breathing bag in accordance with claim 1, wherein the pocket has a flexible configuration in at least some sections.

3. A breathing bag in accordance with claim 1, wherein:
the pocket has a contact section on a surface facing the inner volume;
the bag section comprises a counter-contact section; and
the contact section being contacted by a counter-contact section of the bag section.

4. A breathing bag in accordance with claim 3, wherein the contact section has a projecting releasing component.

5. A breathing bag in accordance with claim 1, wherein the pocket has a tapering configuration along a pocket longitudinal extension, the pocket longitudinal extension extending in the inner volume.

6. A breathing bag in accordance with claim 1, wherein the lever component is a component of the breathing bag and is fastened in an internal receptacle mount, defined by the internal receptacle of the pocket, by a connection in substance.

7. A breathing bag in accordance with claim 6, wherein the lever component is welded or bonded or vulcanized or any combination of welded and bonded and vulcanized to the internal receptacle.

8. A breathing bag in accordance with claim 6, wherein the pocket is a molded product and the lever component is a molded product with the pocket and the lever component manufactured together in a multicomponent injection molding process.

9. A system comprising:
a dispensing valve unit for a closed-circuit respirator, the dispensing valve unit comprising:
a dispensing valve providing a quantity of gas into a breathing circuit of the closed-circuit respirator; and
an actuating unit functionally connected mechanically to the dispensing valve for actuating the dispensing valve;
a lever component functionally connected mechanically to the actuating unit for activating the actuating unit; and
a breathing bag for the closed-circuit respirator, the breathing bag comprising:
a tray section; and
a bag section, wherein the tray section and the bag section enclose an inner volume of variable size and wherein the bag section is configured to dip at least temporarily and at least partially into the tray section, providing a reduction in the size of the inner volume, wherein the tray section comprises a pocket with an internal receptacle for receiving a lever component for actuating the actuating unit of the dispensing valve unit of the closed-circuit respirator, wherein the pocket with the internal receptacle protrudes into the inner volume and the internal receptacle is separated from the inner volume in a gas-tight manner and the internal receptacle is furthermore accessible from an outside of the breathing bag, wherein the lever component is arranged in the internal receptacle of the pocket.

10. A system in accordance with claim 9, wherein the lever component is a component of the actuating unit.

11. A system in accordance with claim 9, wherein the lever component is a component of the breathing bag.

12. A system in accordance with claim 9, wherein the actuating unit is configured for the continuous or at least essentially continuous control of a quantity of gas provided through the dispensing valve, the quantity being a function of a deflection of the lever component.

13. A system in accordance with claim 9, wherein the dispensing valve comprises a junction section, for providing the quantity of gas at a feed point located at a distance from the breathing bag, into a breathing circuit of the closed-circuit respirator.

14. A system in accordance with claim 9, wherein the dispensing valve unit has a fastening section for fastening at a counter-fastening section of a housing of the closed-circuit respirator.

15. A system in accordance with claim 9, wherein the dispensing valve unit comprises a sensor unit for monitoring an actuation of the dispensing valve.

16. A system in accordance with claim 15, wherein the sensor unit comprises at least one of the following sensor components:
   Hall sensor;
   optical sensor;
   motion sensor; and
   gas flow sensor.

17. A system according to claim 9, wherein the system comprises a closed-circuit respirator and further comprises a closed-circuit respirator housing connected to the breathing bag and the dispensing valve unit.

18. A process for mounting a closed-circuit respirator system, the process comprising the steps of:
   providing a dispensing valve unit for a closed-circuit respirator, the dispensing valve unit comprising a dispensing valve providing a quantity of gas into a breathing circuit of the closed-circuit respirator and an actuating unit functionally connected mechanically to the dispensing valve for actuating the dispensing valve;
   providing a lever component functionally connected mechanically to the actuating unit for activating the actuating unit;
   providing a breathing bag for the closed-circuit respirator, the breathing bag comprising a tray section and a bag section, wherein the tray section and the bag section enclose an inner volume of variable size and wherein the bag section is configured to dip at least temporarily and at least partially into the tray section, providing a reduction in the size of the inner volume, wherein the tray section comprises a pocket with an internal receptacle for receiving a lever component for actuating the actuating unit of the dispensing valve unit of the closed-circuit respirator, wherein the pocket with the internal receptacle protrudes into the inner volume and the internal receptacle is separated from the inner volume in a gas-tight manner and the internal receptacle is furthermore accessible from an outside of the breathing bag;
   providing a closed-circuit respirator housing;
   arranging and fastening of the dispensing valve unit and of the lever component in the closed-circuit respirator housing; and
   inserting the breathing bag into the closed-circuit respirator housing by pushing the internal receptacle of the pocket of the breathing bag over the lever component.

19. A process in accordance with claim 18, wherein the lever component is a component of a pre-assembly comprising the actuating unit.

20. A process in accordance with claim 18, wherein the lever component is a component of the breathing bag and the pocket is a molded product and the lever component is a molded product with the pocket and the lever component manufactured together in a multicomponent injection molding process.

* * * * *